United States Patent
Pisilä et al.

(10) Patent No.: US 10,491,971 B2
(45) Date of Patent: Nov. 26, 2019

(54) SENSOR FOR MONITORING AMBIENT CHARACTERISTICS

(71) Applicant: SOLENTUM B.V., Joure (NL)

(72) Inventors: Eero Pisilä, Yppäri (FI); Antti Hintikka, Lelystad (NL)

(73) Assignee: SOLENTUM B.V., Joure (NL)

( * ) Notice: Subject to any disclaimer, the term of this patent is extended or adjusted under 35 U.S.C. 154(b) by 195 days.

(21) Appl. No.: 15/516,591

(22) PCT Filed: Oct. 2, 2015

(86) PCT No.: PCT/FI2015/050662
§ 371 (c)(1),
(2) Date: Apr. 3, 2017

(87) PCT Pub. No.: WO2016/051026
PCT Pub. Date: Apr. 7, 2016

(65) Prior Publication Data
US 2018/0270547 A1   Sep. 20, 2018

(30) Foreign Application Priority Data
Oct. 2, 2014   (FI) .................................... 20145859

(51) Int. Cl.
*G05B 23/02* (2006.01)
*H04Q 9/00* (2006.01)
(Continued)

(52) U.S. Cl.
CPC ............... *H04Q 9/00* (2013.01); *A01F 25/00* (2013.01); *G01D 21/00* (2013.01); *G01N 33/02* (2013.01);
(Continued)

(58) Field of Classification Search
CPC ............ H04Q 9/00; A01F 25/00; H04W 4/30; G01N 33/02; G05B 23/02
See application file for complete search history.

(56) References Cited

U.S. PATENT DOCUMENTS

| 4,745,564 A | 5/1988 | Tennes et al. |
| 7,719,432 B1 | 5/2010 | Hill |

(Continued)

FOREIGN PATENT DOCUMENTS

| CA | 1296426 C | 2/1992 |
| CA | 3 000 793 A1 | 4/2016 |

(Continued)

OTHER PUBLICATIONS

J. Huang et al: "Development of a wireless soil sensor network", American Society of Agricultural and Biological Engineers Annual International Meeting 2008: Jun. 29-Jul. 2, 2008, Providence, Rhode Island, USA, Jun. 29, 2008 (Jun. 29, 2008), pp. 97-105.

(Continued)

*Primary Examiner* — Phung Nguyen
(74) *Attorney, Agent, or Firm* — FisherBroyles, LLP (57) ABSTRACT

A sensor device for monitoring at least one lifecycle of potatoes, at least from planting seed potatoes to stocking the potatoes includes a body dimensioned and shaped to conform to a potato. The body houses electronics of the sensor device and includes a waterproof layer for protecting the electronics when the sensor device is placed underground with the seed potatoes. The electronics includes a wireless communication circuitry providing the sensor device with radio communication capability, at least one processor, and at least one of the following sensors: a humidity sensor; a temperature sensor; and a carbon dioxide sensor. The at least one processor is configured to store measurement data provided by the at least one sensor, and to cause the wireless (Continued)

communication circuitry to transmit the measurement data to another device.

13 Claims, 5 Drawing Sheets

(51) Int. Cl.
    *G01N 33/02*     (2006.01)
    *G08C 21/00*     (2006.01)
    *G01N 33/24*     (2006.01)
    *G01D 21/00*     (2006.01)
    *A01F 25/00*     (2006.01)
    *G05B 15/02*     (2006.01)

(52) U.S. Cl.
    CPC .......... *G01N 33/025* (2013.01); *G01N 33/24* (2013.01); *G01N 33/246* (2013.01); *G05B 15/02* (2013.01); *G08C 21/00* (2013.01); *G01N 2033/245* (2013.01); *H04Q 2209/40* (2013.01); *H04Q 2209/43* (2013.01)

(56) References Cited

U.S. PATENT DOCUMENTS

| | | |
|---|---|---|
| 8,035,403 B1 | 10/2011 | Campbell et al. |
| 8,340,910 B1 | 12/2012 | Magro et al. |
| 2004/0083833 A1 | 5/2004 | Hitt et al. |
| 2004/0226392 A1* | 11/2004 | McNally ............... G01D 21/02 73/866.1 |
| 2005/0127925 A1* | 6/2005 | Staples ............... A01G 25/167 324/694 |
| 2010/0192619 A1* | 8/2010 | Dieter ................... F25D 11/003 62/440 |
| 2014/0313055 A1* | 10/2014 | Warkentin ............... H04Q 9/00 340/870.16 |

FOREIGN PATENT DOCUMENTS

| | | |
|---|---|---|
| CN | 2927659 Y | 8/2007 |
| CN | 101156628 A | 4/2008 |
| CN | 201649757 U | 11/2010 |
| CN | 202064675 U | 12/2011 |
| CN | 103196486 | 7/2013 |
| CN | 203152132 U | 8/2013 |
| CN | 203433329 U | 2/2014 |
| CN | 203562091 U | 4/2014 |
| CN | 107209981 A | 9/2017 |
| DE | 263588 A1 | 1/1989 |
| EP | 0235534 A1 | 9/1987 |
| EP | 3 201 892 A1 | 8/2017 |
| JP | S6413465 A | 1/1989 |
| WO | WO199958983 A1 | 11/1999 |
| WO | WO200241095 A1 | 5/2002 |
| WO | WO2004080615 A2 | 9/2004 |
| WO | 2016/051026 A1 | 4/2016 |

OTHER PUBLICATIONS

Jeonghwan Hwang et al: "Study on an Agricultural Environment Monitoring Server System using Wireless Sensor Networks", Sensors, vol . 10, No. 12, Dec. 8, 2010 (Dec. 8, 2010), pp. 11189-11211.
Juan Lopez et al: "Development of a Sensor Node for Precision Horticulture", Sensors, vol. 9, No. 5, Apr. 28, 2009 (Apr. 28, 2009), pp. 3240-3255.
Database WPI, Week 201373, Thomson Scientific, London, GB; AN 2013-T23198, XP002783374, & CN 103 196 486 A (Kunming Vim Technology Co Ltd) Jul. 10, 2013 (Jul. 10, 2013) abstract.
Kshitij Shinghal et al: "Wireless sensor networks in agriculture: for potato farming", Journal of Cleaner Production, vol. 2, No. 8, Aug. 1, 2010 (Aug. 1, 2010), pp. 3955-3963.
European Search Report issued in European Application No. EP 15846537 dated Jul. 26, 2018.
Search Report issued in corresponding International Application, PCT/FI2015/050662, dated Dec. 18, 2015.
Search Report issued in corresponding Finnish priority application, FI20145859, dated May 27, 2015.
Muller, I. et al. "Wireless instrumented sphere for three-dimensional force sensing", IEEE Sensors Applications Symposium, New Orleans, USA, Feb. 2009, pp. 153-157.
Hein, T. "Using real-time data to reduce fruit and vegetable bruising." Fruit & Vegetable Magazine, vol. 64 No. 4, Apr. 2008, pp. 16-17.
Mampentzidou, I. et al. "Basic guidelines for deploying wireless sensor networks in agriculture", The 4th International Congress on Ultra Modern Telecommunications and Control Systems and Workshops (ICUMT), St. Petersburg, Russia, Oct. 2012, pp. 864-869.
Lishman, Martin "Potato Quality Equipment", URL: http://www.martinlishman.com/agricultural/home/potato-quality-equipmentltuberlog, Tuberlog Instruction Manual and User Guide, distributed by Martin Lishman, May 2014, pp. 1-12.
First Office Action received for Chinese Patent Application Serial No. 201580065130.6 dated Jul. 3, 2019, 11 pages (including English Translation).
International Preliminary Report on Patentability received for PCT Application Serial No. PCT/FI2015/050662 dated Apr. 13, 2017, 10 pages.

\* cited by examiner

SENSOR FOR MONITORING AMBIENT CHARACTERISTICS

CROSS-REFERENCE TO RELATED APPLICATION

This application is a National Stage application of International Application No. PCT/FI2015/050662, filed Oct. 2, 2015, which claims priority to Finnish Application No. 20145859, filed Oct. 2, 2014, which are incorporated by reference herein their entirety.

BACKGROUND

Field

The invention relates to a sensor device and, particularly, to a sensor device for monitoring environmental properties related to a lifecycle of a vegetable.

BRIEF DESCRIPTION

There exist commercially available sensor devices that are configured to monitor environmental or ambient characteristics such as humidity or temperature. Provided with suitable technical solutions, such sensors may be used in various applications.

SUMMARY

An aspect of the invention is defined by the subject matter of the independent claims.

Embodiments are defined in the dependent claims.

BRIEF DESCRIPTION OF THE DRAWINGS

In the following the invention will be described in greater detail by means of preferred embodiments with reference to the accompanying drawings, in which.

DETAILED DESCRIPTION

The following embodiments are exemplary. Although the specification may refer to "an", "one", or "some" embodiment(s) in several locations, this does not necessarily mean that each such reference is to the same embodiment(s), or that the feature only applies to a single embodiment. Single features of different embodiments may also be combined to provide other embodiments. Furthermore, words "comprising" and "including" should be understood as not limiting the described embodiments to consist of only those features that have been mentioned and such embodiments may contain also features/structures that have not been specifically mentioned.

Figure 1:
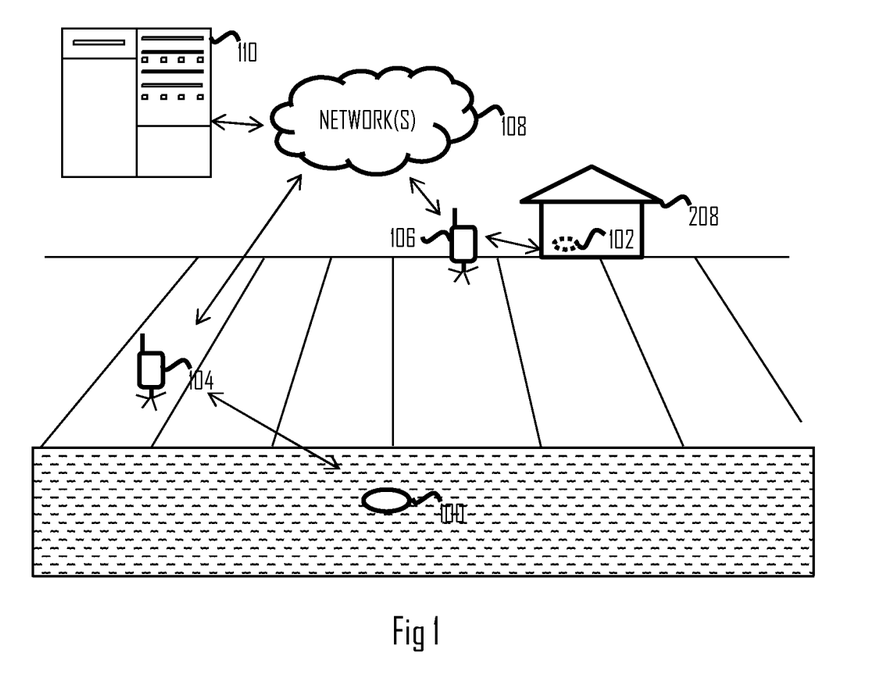
FIG. 1 illustrates a scenario to which embodiments of the invention may be applied.

FIG. 1 illustrates an example of a scenario to which embodiments of the invention may be applied. Referring to FIG. 1, a system according to an embodiment of the invention comprises at least one sensor device 100, 102 configured to measure ambient characteristics of an environment of a potato with respect to one or more of planting, growing, harvesting, transporting, and stocking the potato. The sensor device is suitable for being disposed with seed potatoes when the seed potatoes are gathered and selected for planting and for experiencing the same environmental properties that the potato experiences during its lifecycle from planting throughout the growth season to harvesting, stocking and transportation. The sensor device may be separated from the potatoes at a determined stage, e.g. when the potatoes are retrieved from the storage for transportation to a food processing industry or at a beginning of the food processing process. The lifetime of the sensor device may thus be longer than the lifetime of the potato so the sensor device may be practically used for monitoring a plurality of lifecycles of the potatoes. This enables detection of characteristics of the environment of the potatoes over a timespan longer than a single lifecycle of the potato, which allows comparison between environments of different crops. For example, the sensor device that has travelled together with a first crop from the planting to the storage may be picked among seed potatoes selected from the first crop and planted together with the seed potatoes that form a second, subsequent crop. As a consequence, measurement data acquired with respect to the first crop may be combined with measurement data acquired with respect to the second crop. This may provide important information on the effect of a growing or storing environment of a seed potato on the next crop.

As illustrated in FIG. 1, the sensor device 100, 102 is suitable for being placed underground for the duration the potato crop grows, being harvested together with the crop, and being transported and stored in a stockpile 208 together with the crop. In order to provide the sensor device 100, 102 with a lifetime of the lifecycle of the potato, the sensor device may be configured to employ short-range wireless communications such as Bluetooth Smart known also as Bluetooth Low Energy. Other low energy wireless communication technologies employed conventionally with sensor devices may be equally applicable. One or more wireless router devices 104, 106 may be disposed within the communication distance of the sensor devices 100, 102. The wireless router devices 104, 106 may be designed for indoor and/or outdoor use, e.g. the wireless router device 104 may be disposed in the field where the seed potatoes have been planted while the wireless router device 106 may be disposed in the stockpile indoors. Similar router devices may be disposed in a truck or container transporting the potatoes to enable monitoring the transporting of the potatoes. When a plurality of sensor devices is distributed in a field, one or more router devices may be deployed to provide radio coverage to all sensor devices. The plurality of sensor devices deployed in the same field may be used to determine whether or not there are differences in the growing environment within the same field and/or to compensate for breaking and/or malfunctioning of individual sensor devices. The number of wireless router devices needed to provide the overall coverage may depend on the implementation. The wireless router devices may support the short-range wireless communication technology employed by the sensor devices 100, 102 and, additionally, a long-range wireless communication technology such as a cellular communication technology. Examples of the cellular communication technology include the GSM (Global System for Mobile Communications), UMTS (Universal Mobile Telecommunication System), and LTE (Long-Term Evolution). The long-range wireless communication technology may be used to provide the wireless router device 104, 106 with a data connection to a server computer 110 storing a database for the measurement data measured by the sensor devices 100, 102. The data connection may be routed through one or more wireless networks 108 comprising a radio access network and a core network of a cellular communication system and the Internet. The server computer 110 may be connected to the Internet via a local area network and/or via a broadband access such as a digital subscriber line (DSL). The router device 104, 106 may be battery-powered, and the battery may be dimensioned with more battery capacity than a battery of the sensor device 100, 102. The battery of the router device may be replaceable and/or rechargeable. Accordingly, the router device 104, 106 may employ higher transmit powers and more power-consuming communication protocols than the sensor device 100, 102. This enable reliable communications even when the potatoes grow stalks and leaves that attenuate radio signals.

In an embodiment a hub device may be provided to serve as a hub for a plurality of router devices. In such an embodiment, the router devices may communicate with the hub device by employing a short-to-medium range communication protocol, e.g. Class 1 of the Bluetooth protocol, and the hub device may employ the long-range communication protocol such as the cellular communication protocol.

Figure 2:
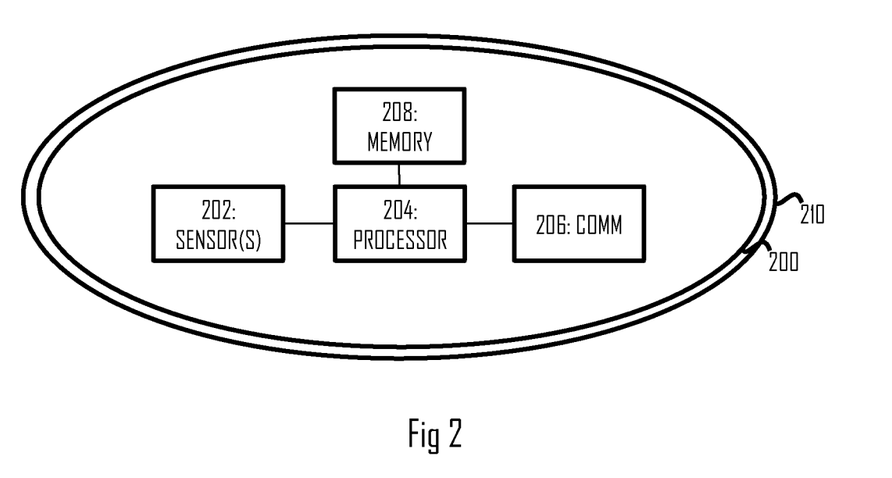
FIGS. 2 to 4 illustrate sensors devices according to some embodiments of the invention.

Let us now describe the sensor device 100, 102 in greater detail with reference to FIG. 2. The sensor device 100, 102 is designed for use in monitoring at least one lifecycle of potatoes, at least from planting seed potatoes to stocking the potatoes. The sensor device comprises a body 210 dimensioned and shaped to conform to the potato. The shape of the body or its cross-section may be substantially oval but, in some embodiments, the body may resemble a deformed oval form to imitate the non-uniform general shape of the potatoes. The material of the body may be selected such that the weight of the sensor device matches the weight of the potato, e.g. between 100 and 200 grams. The material of the body may further be selected such that it represents the consistency of the potato, e.g. resiliency of the body may correspond to the resiliency of the potato. The body 210 may be designed such that it corresponds to the mechanical structure and/or surface of a potato. The length of the body 210 may be in the range of four to ten centimetres, for example. The width of the body 210 may be in the range of three to six centimetres. Such design of the sensor device provides for that the sensor device behaves like a real potato and experiences similar impulses as the real potato. The body 210 may provide a housing enclosing electronics of the sensor device 100, 102 and comprising a waterproof layer 200 for protecting the electronics when the sensor device 100, 102 is placed underground with the seed potatoes such as the sensor device 100 illustrated in FIG. 1. The electronics may be integrated into the body 210. The electronics of the sensor device 100, 102 may comprise a wireless communication circuitry 206 providing the sensor device 100, 102 with radio communication capability, at least one processor 204, and at least one of the following sensors 202: a humidity sensor, a temperature sensor, and a carbon dioxide sensor. The at least one processor is configured to store measurement data provided by the at least one sensor 202 and to cause the wireless communication circuitry 206 to transmit the measurement data to another device. The other device may be the wireless router device 104, 106.

The electronics may further comprise at least one memory 208 storing a computer program code configuring the at least one processor 204. The memory 208 may further provide a temporary storage for the measurement data, and the processor 204 may use the memory 208 to log the measurement data acquired from the sensor(s) 202 before the measurement data is transmitted through the communication circuitry 206.

In an embodiment, the waterproof layer 200 completely encloses the electronics. In an embodiment, the waterproof layer 200 comprises or consists of a waterproof, breathable fabric membrane. An example of such a membrane is a Gore Tex® fabric membrane.

In an embodiment, the body is made of a rigid material such as plastics, rubber, or a composite fibre material. The material may be mechanically durable and transparent to radio waves. The electronics may be embedded on a circuit board. In an embodiment, the body is made breathable by the appropriate selection of the material such that the body is capable of transferring changes in ambient properties into the body where the sensors are provided. Accordingly, the material of the body may be designed such that it exchanges carbon dioxide and/or humidity properties between the exterior and the interior of the body.

Figure 3:
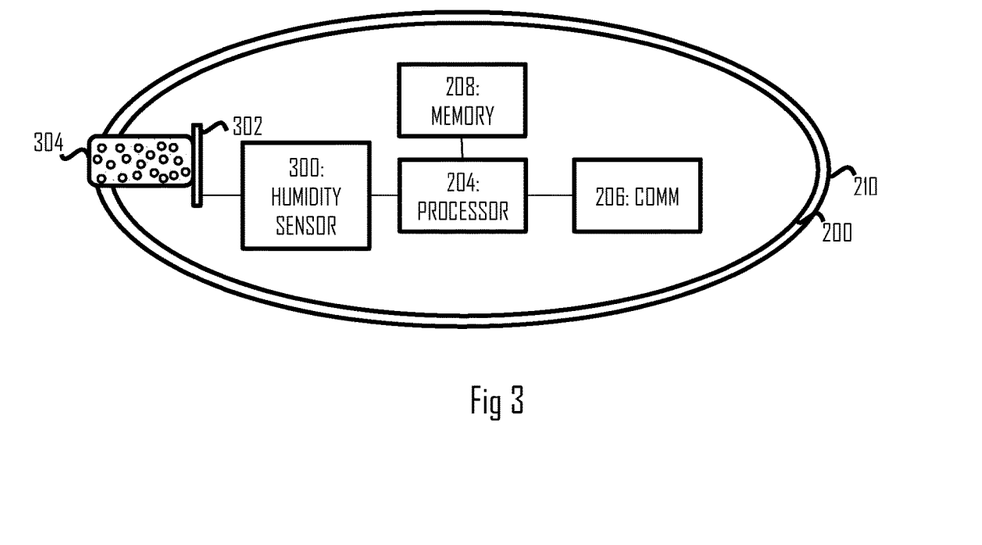

In an embodiment, the sensor (s) 202 comprises at least the humidity sensor. FIG. 3 illustrates such an embodiment. In this embodiment, the waterproof layer 200 may enclose the electronics only partially. Because humidity needs to be exchanged between the exterior of the sensor device 100, 102 and the humidity sensor, at least a part of the waterproof layer 200 may be penetrated by a humidity exchanging member 304 made of a water-irresistible material. The humidity exchanging member 304 may be made of porous or woven material made of plastics, composite fibres, metallic fibres. The humidity exchanging member 304 may be disposed at a location of the humidity sensor 300 or an electrode 302 of the humidity exchanging sensor 300 and arranged to convey humidity from an exterior of the sensor device 100, 102 to the humidity sensor 300.

In another embodiment, the electrode 302 may be arranged to an exterior of the waterproof layer 200. In such an embodiment, the electrode 302 or a signal line connecting the electrode 302 with other electronics of the humidity sensor 300 may penetrate the waterproof layer 200. The other electronics of the humidity sensor 300 may comprise circuits such as an amplifier circuit, a filter circuit, and an analogue-to-digital (A/D) converter circuit.

In an embodiment, the humidity exchanging member 304 is attached to the body 210 in a detachable manner so that the humidity exchanging member 304 is replaceable. The detachable humidity exchanging member may also serve as a maintenance hatch providing access to the electronics. The electronics may comprise a replaceable battery which may be replaced through the maintenance hatch.

Figure 4:
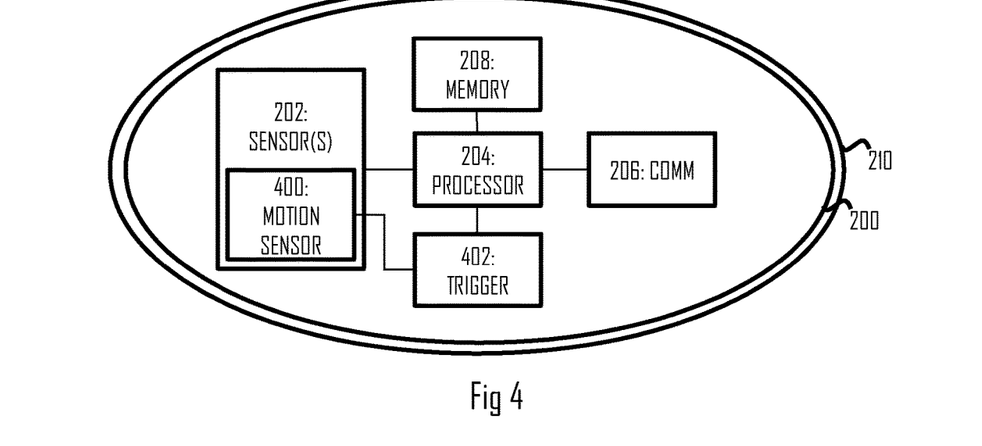

In an embodiment, the sensor(s) 202 comprise a motion sensor 400. The motion sensor 400 may be used to measure acceleration induced to the sensor device 100, 102 and to the potatoes during planting, harvesting, and/or transportation. Motion measurement data provided by the motion sensors may provide important information on possible mishandling of the potatoes during the transportation, for example. It may also help to improve machines used for handling the potatoes. Considering the fact that the sensor device is most of the time underground or in the storage, it may not be feasible to acquire and store the motion measurement data in a similar manner as the other measurement data. The motion is an event-based phenomenon and localizes to certain occasions when the potatoes are manipulated. The motion sensor 400 may comprise an accelerometer or a plurality of accelerometers, for example, arranged to convert mechanic energy into an electric signal. A three-dimensional accelerometer may be employed. An output of the motion sensor 400 may be coupled to a trigger circuitry 402, wherein the trigger circuitry 402 is arranged, in response to an input signal received from the motion sensor, to wake up the at least one processor 204 to perform measurements. In some embodiments, the trigger circuitry 402 may be comprised in the processor 204. The trigger circuitry 402 may wake the processor to store the motion data measured by the motion sensor 400. In this manner, the motion measurement data may be acquired and stored in an event-based manner rather than a time-based manner. Accordingly, the motion measurement data may be stored only when mechanical forces are applied to the sensor device 100, 102 and sensed by the motion sensor 400.

Figure 5:
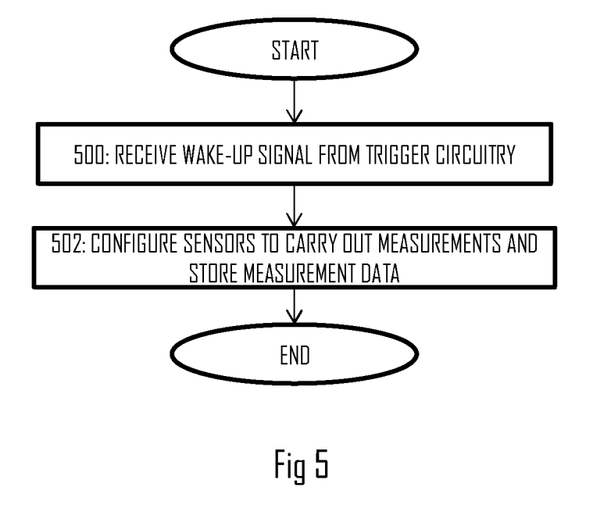
FIG. 5 is a flow diagram of a process for triggering measurements in the sensor device according to an embodiment of the invention.

In an embodiment, the processor may configure the other sensors to perform the measurements and acquire and store the measurement data in a time-based manner, e.g. periodically. FIG. 5 illustrates a flow diagram of such a process executed by the at least one processor 204. Upon receiving the wake-up signal from the trigger circuitry 402 in block 500, the processor 204 may be configured to acquire additional event-based measurement data from the other sensors at the time instant or a time interval when the motion sensor 400 indicates that the sensor device is being moved (block 502). In this manner, the processor 204 is able to store even very momentary changes in the temperature, humidity, or carbon dioxide level that might have otherwise been missed because of long periodicity of measurements, for example. Block 502 may comprise configuring the sensor(s) to measure the measurement data with a higher periodicity or, in some embodiments, constantly, for the duration the measurement data acquired from the motion sensor 400 indicates accelerations that exceed a determined acceleration threshold.

Figure 6:
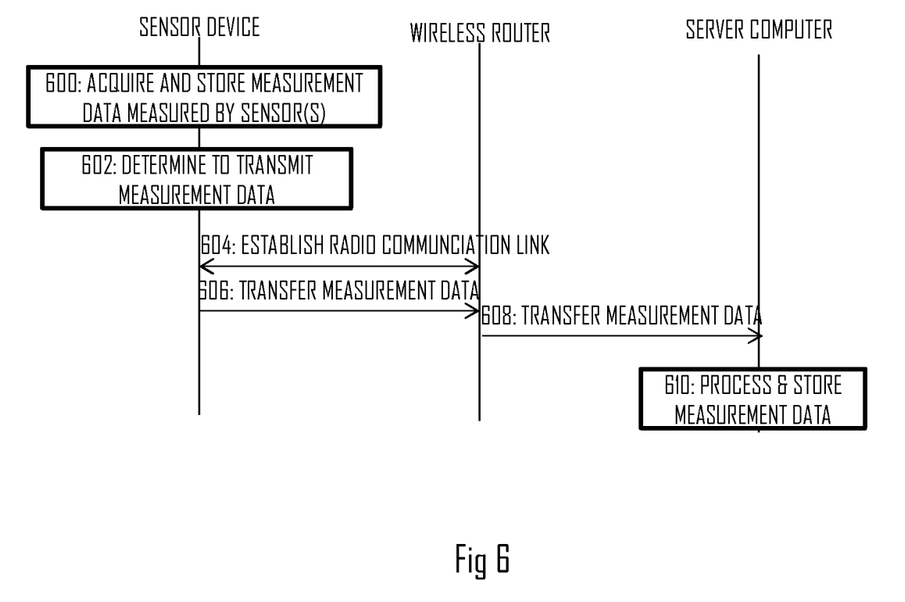
FIG. 6 is a signalling diagram illustrating a process for transferring measurement data to a server computer.

Let us now describe a procedure for transferring the measurement data from the sensor device to a server computer storing a database for the measurement data. The sensor device may acquire and store temporarily the measurement data in the above-described manner in block 600. The processor may be configured to execute block 600 with a determined periodicity and/or in the event-based manner. In block 602, the processor 204 of the sensor device determines to transmit the measurement data. The processor 204 may be configured to transmit the measurement data periodically, e.g. every 24 hours. The transmission periodicity may be longer than the measurement periodicity. Upon determining to transmit the measurement data, the processor 204 may configure the wireless communication circuitry to establish a radio communication link with a wireless router device (step 604) the established radio communication link may comprise a short-range radio communication link such as a Bluetooth link. Upon establishing the link, the sensor device may transmit the stored measurement data to the wireless router device in step 606. Upon transmitting the measurement data, the sensor device may delete the measurement data from its memory. The wireless router device may receive the measurement data from the sensor device in step 606 and forward the measurement data to the server computer in step 608. Upon receiving the measurement data through the wireless router device, the server computer may store the received measurement data in the database in block 610. The server computer may store the measurement data received from a given sensor device in the same record associated with the sensor device and labelled with an identifier of the sensor device. The record may further store information on the current location of the sensor device. The location of the sensor device may be determined on the basis of a router device 104, 106 that forwarded the measurement data. Each router device 104, 106 may be configured to add its identifier to a data packet comprising the measurement data and forwarded from the sensor device 100, 102 to the server computer 110. The locations of the router devices 104, 106 may be stored in the server computer in connection with setting up the system. In another embodiment, the router device may be provided with a satellite positioning receiver and configured to add location coordinates determined by using the satellite positioning receiver into the data packet. The identifier in combination with the known location and the location coordinates are both embodiments of a location label transmitted to the server computer. Accordingly, the server computer may determine the location of the sensor device on the basis of the location label received from the router device currently associated with the sensor device. The location label may comprise real location coordinates measured by the satellite positioning receiver comprised in the router device, or the location determined from the location label may comprise a classification of the location in terms of "field", "storage", "transport", "food processing plant". This enables determining the state of the lifecycle of the potato upon measuring the measurement data. The database may be accessible by client computers through the Internet, for example. The database may be accessible to farmers, seed tuber breeders, research institutes, authorities, etc.

In an embodiment, the positioning of the sensor device may be linked to the operation of the motion sensor 400 comprised in the sensor device. Upon determining on the basis of measurement data acquired from the motion sensor 400 that the potato is moving, e.g. the measurement data shows acceleration exceeding a determined threshold, the processor 204 may configure the communication circuitry 206 to generate a message and transmit the message to the router device 104, 106. The message may comprise an instruction to measure the current location. Upon receiving the message, the router device 104, 106 may be configured to configure its positioning circuitry, e.g. a satellite positioning receiver, to measure the current location of the router device. The location may then be transferred to the server computer in connection with an identifier of the sensor device. The location may be defined in the form of location coordinates. As a consequence, the server computer may store the location of the sensor device where the sensor device experienced motion. This information may be used during the planting phase. For example, a planting vehicle may comprise the router device and, upon receiving the instruction from the sensor device when the sensor device is being placed underground and experiencing motion causing the transmission of the instruction, the router device of the planting vehicle may determine the location to which the sensor device is planted. This location is then stored in the database. When disposing the router devices to the field to carry out the forwarding of the measurement data while the potatoes are growing, this location may be used to determine the location to which to dispose the router device. As a consequence, the router device will be disposed close to the sensor device, thus enabling reliable communication link.

In another embodiment, the router device may trigger the execution of block 602 in the sensor device. For example, the router device may transmit an activation signal that, when received by the sensor device, triggers the execution of block 602. As an example application related to the growth season of the potato, a vehicle carrying the router device may travel across the field, e.g. a helicopter or a crop duster/sprayer vehicle. The router device may be configured to constantly or periodically transmit the activation signal having a determined transmission range that corresponds to the transmission range of the sensor device. Through the use of the activation signal, the measurement data may be collected from the sensor devices while the vehicle is used for its main purpose. The positioning of the sensor device described in the previous paragraph may be used in this embodiment, too, by determining a location in which the measurement data from the sensor device is acquired in the router device.

Instead of the activation signal, another proximity-based detection may be used to trigger the execution of block 602. For example, the above-described motion sensor may be used to trigger block 602. The vehicle may cause tremors in the ground that can be sensed by the motion sensor. Upon detecting motion exceeding a determined threshold, e.g. motion representing tremors or displacement of the sensor device, the sensor device may trigger execution of block 602 and carry out transmission of the measurement data.

In an embodiment, upon failing in establishing a communication connection with a router device 104, 106, the sensor device 100, 102 may be configured to store the measurement data and retry the communication connection after a determined period of time.

In an embodiment, the transmissions of the sensor device are broadcast or advertisement transmissions that require no establishment of a communication connection with the router device. For example, Bluetooth Smart employs such a transmission type.

Figure 7:
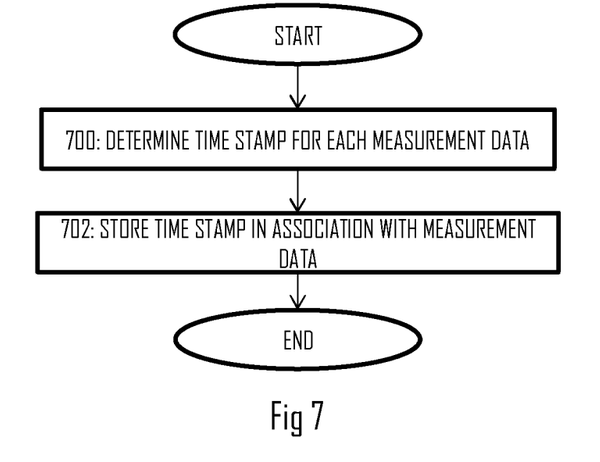
FIG. 7 is a flow diagram of a process for time-stamping measurement data according to an embodiment of the invention.

In an embodiment, the router device 104, 106 comprises at least one sensor configured to measure ambient characteristics such as temperature, air humidity, ground humidity, carbon dioxide levels, and/or oxygen levels. Upon receiving a data packet comprising measurement data from a sensor device, the router device may forward the measurement data to the server computer together with measurement data measured by the at least one sensor of the router device. In another embodiment, the router device may transmit the measurement data measured by the at least one sensor independently of the reception of the measurement data from the sensor device. Providing additional sensors in the router device 104, 106 improves the accuracy of the measured ambient characteristics of the potatoes. FIG. 7 illustrates a flow diagram of a process for labelling the measurement data in the server computer or in the sensor device according to an embodiment. Referring to FIG. 7, the server computer is configured determine a time label for each piece of received measurement data (block 700) and to store the time label in association with said each piece of measurement data (block 702). The time label may be attached to the measurement data in the sensor device to better correspond with the actual measurement timing. However, the time label may be added to the measurement data in the server computer. The sensor device and/or the server computer may comprise a clock or a timer arranged to measure the time and the time label may be acquired from the time measured with the clock or the timer.

Figure 8:
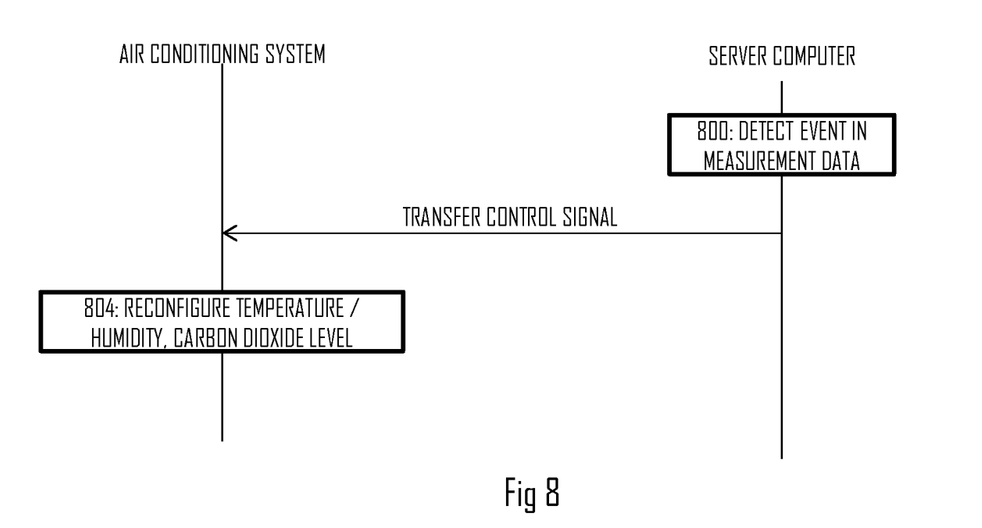
FIG. 8 is signalling diagram of using the sensor device to control an air conditioning system of a stockpile according to an embodiment of the invention.

In an embodiment, the server computer is connected to an automated system managing characteristics of a facility where the potatoes and the sensor device are stored. The connection may be a control type of connection established through one or more communication networks. The facility may be a stockpile or a container. The sensor device may be used to sense the humidity, temperature, and/or carbon dioxide levels experienced by the potatoes and, as a consequence, serve as a more accurate sensor than a sensor provided in the structures of the stockpile or the container. The server computer may acquire the measurement data from the sensor device comprising one or more of the above-described sensors in the above-described manner. FIG. 8 illustrates an embodiment of a procedure for controlling the automated system, e.g. an air conditioning system of the stockpile or the container. Referring to FIG. 8, the server computer may be configured to analyse the received measurement data and attempt to detect one or more events in the measurement data. The server computer may compare measurement values of received humidity measurement data, temperature measurement data, and/or carbon dioxide measurement data with corresponding one or more threshold levels. If a determined event is detected in the received measurement data (block 800), the server computer may as a response to the detection of the determined event output a control signal so as to reconfigure the air conditioning system. For example, if the temperature measurement data indicates temperature below a minimum temperature threshold, the control signal may cause the automated system to increase the temperature. If the temperature measurement data indicates temperature above a maximum temperature threshold, the control signal may cause the automated system to decrease the temperature. If the humidity measurement data indicates humidity below a minimum humidity threshold, the control signal may cause the automated system to increase the humidity. If the humidity measurement data indicates humidity above a maximum humidity threshold, the control signal may cause the automated system to decrease the humidity. If the carbon dioxide measurement data indicates a carbon dioxide level below a minimum carbon dioxide level threshold, the control signal may cause the automated system to increase the carbon dioxide level. If the carbon dioxide measurement data indicates a carbon dioxide level above a maximum carbon dioxide level threshold, the control signal may cause the automated system to decrease the carbon dioxide level. If the motion measurement data indicates that the potatoes experience accelerations above an acceleration threshold, the server computer may output an alarm signal to indicate, for example, that a contained is loose during the transport. Block 800 may further comprise storing information on the detected event.

Figure 9:
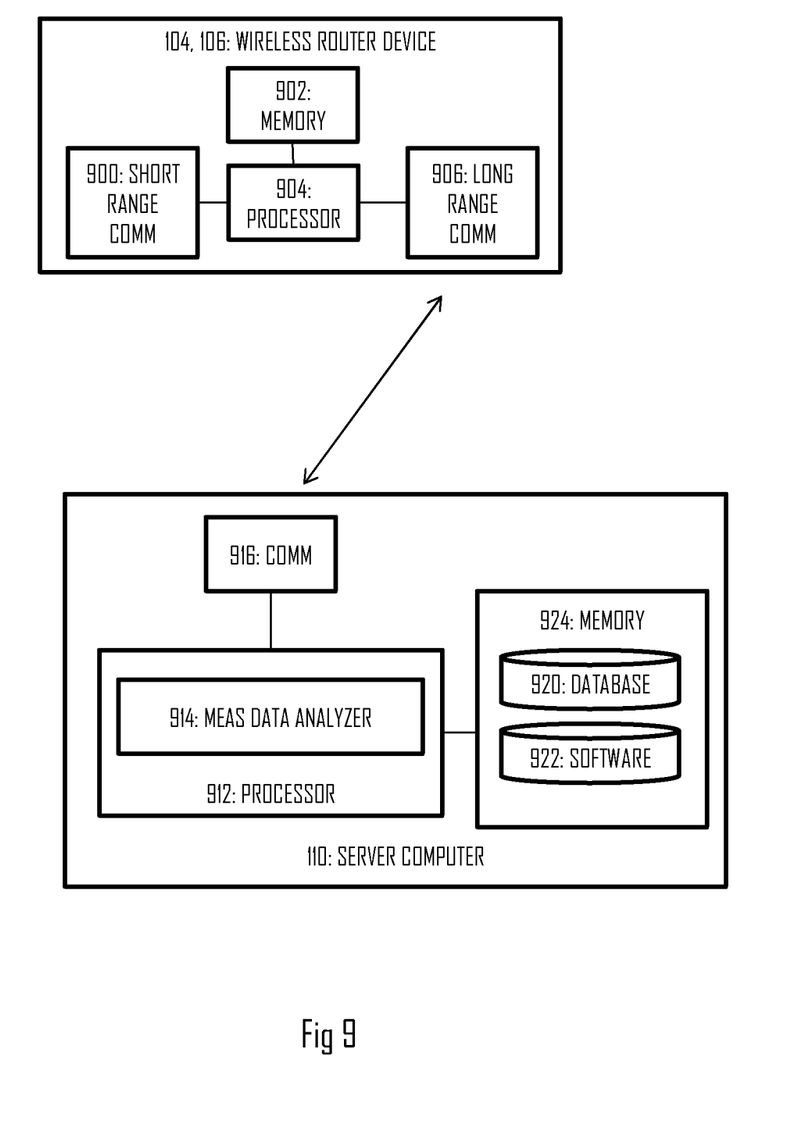
FIG. 9 illustrates structures of a wireless router device and a server computer according to an embodiment of the invention.

FIG. 9 illustrates block diagrams of the server computer 110 and the wireless router device 104, 106 according to some embodiments of the invention. Referring to FIG. 9, the wireless router device 104, 106 comprises a short range communication circuitry 900 configured to establish the above-described short range radio communication link with one or more sensor devices and to receive the measurement data from the sensor device(s). The short range communication circuitry 900 may be connected to a processor 904 configured to process the measurement data and store it temporarily in a memory 902, e.g. a non-volatile memory or a random access memory. Upon determining to transmit the stored measurement data to the server computer 110, the processor 904 may retrieve the stored measurement data from the memory and configure a long range communication circuitry 906 to transmit the measurement data to the server computer over a communication connection comprising wireless and/or wired communication links between the devices 104/106, 110. The server computer 110 may comprise a communication circuitry 916 configured to receive the measurement data from one or more wireless router devices and, as a consequence, from one or more sensor devices. The communication circuitry 916 may further establish the control connection to the above-described automated system. The received measurement data may be processed by a processor 912 comprising a measurement data analyser circuitry 914. The processor 912 may be configured to store the received measurement data in a database 920 stored in a memory 924. The memory 924 may further store one or more computer program products 922 defining the functions executed by the processor 912 and the measurement data analyser circuitry 914. The measurement data analyser circuitry 914 may be configured to search for the above-described events in the measurement data, e.g. execute block 800.

As described above, the system according to the described embodiments provide the measurement data that spans to one or more potato lifecycles. The acquired measurement data may be compared with visual inspection of the potatoes to determine which ambient characteristics affect the size of the potato, the thickness of the jacket, etc. The measurement data may be used to determine a correct timing for fertilizing, which may increase the crops significantly. The system may be used for educational purposes to illustrate characteristics of the growing and storage environments. The system may further be used to detect and pinpoint when and where unexpected events have occurred. For example, the embodiment where the mechanical force applied to the sensor device causes the measurements may be used to detect when and where a container has fallen or broken during a transport of the potatoes and the sensor device.

As used in this application, the term 'circuitry' refers to all of the following: (a) hardware-only circuit implementations such as implementations in only analog and/or digital circuitry; (b) combinations of circuits and software and/or firmware, such as (as applicable): (i) a combination of processor(s) or processor cores; or (ii) portions of processor(s)/software including digital signal processor(s), software, and at least one memory that work together to cause an apparatus to perform specific functions; and (c) circuits, such as a microprocessor(s) or a portion of a microprocessor(s), that require software or firmware for operation, even if the software or firmware is not physically present.

This definition of 'circuitry' applies to all uses of this term in this application. As a further example, as used in this application, the term "circuitry" would also cover an implementation of merely a processor (or multiple processors) or portion of a processor, e.g. one core of a multi-core processor, and its (or their) accompanying software and/or firmware. The term "circuitry" would also cover, for example and if applicable to the particular element, a baseband integrated circuit, an application-specific integrated circuit (ASIC), and/or a field-programmable grid array (FPGA) circuit for the apparatus according to an embodiment of the invention.

The processes or methods described in connection with FIGS. 1 to 8 may also be carried out in the form of a computer process defined by a computer program. The computer program may be in source code form, object code form, or in some intermediate form, and it may be stored in some sort of carrier, which may be any entity or device capable of carrying the program. Such carriers include transitory and/or non-transitory computer media, e.g. a record medium, computer memory, read-only memory, electrical carrier signal, telecommunications signal, and software distribution package. Depending on the processing power needed, the computer program may be executed in a single electronic digital processing unit or it may be distributed amongst a number of processing units.

It will be obvious to a person skilled in the art that, as the technology advances, the inventive concept can be implemented in various ways. The invention and its embodiments are not limited to the examples described above but may vary within the scope of the claims.

What is claimed is:

1. A sensor device, comprising:
   a body dimensioned and shaped to conform to a potato, the body housing electronics of the sensor device and comprising a waterproof layer for protecting the electronics when the sensor device is placed underground with seed potatoes;
   said electronics being configured for monitoring potatoes from planting the seed potatoes to stocking the potatoes, and for determining, based in part on the body of the sensor device, an effect of a growing environment and a storing environment of the seed potatoes on a subsequent crop; and
   said electronics comprising a wireless communication circuitry providing the sensor device with radio communication capability, at least one processor, and at least one of the following sensors: a humidity sensor, a temperature sensor, and a carbon dioxide sensor, wherein the at least one processor is configured to store measurement data provided by the at least one sensor and to cause the wireless communication circuitry to transmit the measurement data to another device.

2. The sensor device of claim 1, comprising the humidity sensor and further comprising a humidity exchanging member made of a water-irresistible material and arranged to penetrate the water-proof layer and at a location of the humidity sensor and arranged to convey humidity from an exterior of the sensor device to the humidity sensor.

3. The sensor device of claim 2, wherein the water-irresistible material of the humidity exchanging member is porous material.

4. The sensor device of claim 2, wherein the humidity exchanging member is attached to the body in a replaceable manner and serves as a maintenance hatch providing access to the electronics.

5. The sensor device of claim 1, comprising the humidity sensor, the temperature sensor, and the carbon dioxide sensor.

6. The sensor device of claim 1, wherein the waterproof layer comprises a waterproof, breathable fabric membrane.

7. The sensor device of claim 1, further comprising a motion sensor and a trigger circuitry coupled with an output of the motion sensor, wherein the trigger circuitry is arranged, in response to an input signal received from the motion sensor, to wake up the at least one processor to perform measurements by acquiring additional event-based measurement data from at least one sensor other than the motion sensor at a time instant or a time interval when the motion sensor indicates that the sensor device is being moved.

8. The sensor device of claim 1, further comprising a motion sensor configured to measure acceleration induced to the sensor device, wherein the at least one processor is configured, upon determining on the basis of measurement data acquired from the motion sensor that the sensor device is moving, to configure the communication circuitry to generate and transmit a message to a router device having a radio communication link with the sensor device, the message comprising an instruction to measure a current location of the router device.

9. The sensor device of claim 1, wherein the at least one processor is configured to determine a time label for each piece of received measurement data and to store the time label in association with said each piece of measurement data.

10. The sensor device of claim 1, wherein the body comprises breathable material such that the body is capable of transferring changes in ambient carbon dioxide and/or humidity from an exterior of the body to an interior of the body.

11. A system, comprising:
at least one sensor device comprising electronics of at least one of a humidity sensor, a temperature sensor, and a carbon dioxide sensor, and further comprising a body dimensioned and shaped to conform to a potato, the body housing the electronics of the sensor device and comprising a waterproof layer for protecting the electronics when the sensor device is placed underground with seed potatoes, said electronics being configured for monitoring potatoes from planting the seed potatoes to stocking the potatoes, and for determining, based in part on the body of the sensor device, an effect of a growing environment and a storing environment of the seed potatoes on a subsequent crop;
a server computer; and
a wireless router device arranged to establish a radio communication link with the sensor device, to receive measurement data from the at least one sensor device, and to forward the measurement data to the server computer,
the server computer comprising at least one processor and at least one memory storing a database for the measurement data, wherein the processor is configured to receive the measurement data through the wireless router device and to store the received measurement data in the database.

12. The system of claim 11, wherein the server computer is configured to determine a location label for each piece of received measurement data and to store the location label in association with said each piece of measurement data in said database.

13. The system of claim 11, wherein the server computer is arranged to establish a control connection to an air conditioning system installed to a stockpile storing said potatoes, and wherein the processor is configured to detect a determined event in the received measurement data and, as a response to the detection of the determined event, output a control signal so as to reconfigure the air conditioning system.

* * * * *

UNITED STATES PATENT AND TRADEMARK OFFICE
CERTIFICATE OF CORRECTION

PATENT NO.         : 10,491,971 B2
APPLICATION NO.    : 15/516591
DATED              : November 26, 2019
INVENTOR(S)        : Eero Pisilä and Antti Hintikka

Page 1 of 1

It is certified that error appears in the above-identified patent and that said Letters Patent is hereby corrected as shown below:

On the Title Page

Column 1, Line 5, for the country of the inventor Antti Hintikka reads "FINLAND", and should read --NETHERLANDS--

Signed and Sealed this
Twenty-fourth Day of December, 2019

Andrei Iancu
*Director of the United States Patent and Trademark Office*